United States Patent [19]

Revankar et al.

[11] 4,093,624
[45] June 6, 1978

[54] 1,2,4-THIADIAZOLIDINE-3,5-DIONE

[75] Inventors: Ganapathi R. Revankar; Roland K. Robins, both of Santa Ana, Calif.

[73] Assignee: ICN Pharmaceuticals, Inc., Irvine, Calif.

[21] Appl. No.: 763,913

[22] Filed: Jan. 31, 1977

[51] Int. Cl.² .......................................... C07D 285/08
[52] U.S. Cl. ...................... 260/302 D; 260/306.8 D; 424/180; 424/270; 536/23
[58] Field of Search ..................... 260/302 D Primary Examiner—Richard J. Gallagher
Attorney, Agent, or Firm—K. H. Boswell

[57] ABSTRACT

Compounds of the structure

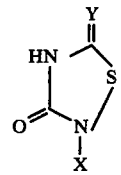

wherein Y is O, NH or NAc; X is H, β-D-ribofuranosyl or 2,3,5-tri-O-Ac-β-D-ribofuranosyl and Ac is acetyl; are useful as antimicrobal agent.

1 Claim, No Drawings

1,2,4-THIADIAZOLIDINE-3,5-DIONE

BACKGROUND OF THE INVENTION

In recent years numerous antimicrobial agents have been developed to combat infections caused by bacteria and fungi, however, because of the development of resistant strains of these organisms and because of the limited spectrum of activity of the presently available drugs there exists a need for new antimicrobial agents. Generally agents which show antibacterial activity do not show antimycologic activity. Further even amoung the antimycologic agents there exists delineated spectrum of activity, that is agents which are active against yeast are not active against molds and visa versa.

Certain thiazole C-nucleosides have been reported by M. Fuertes etal, *J. Carbohydrates, Nucleosides and Nucleotides*, 2, 277–280 (1975). We have reported on certain compounds of the invention in the *Journal of Heterocyclic Chemistry*, 13, 169 (1976), the disclosure of which is expressly incorporated herein by reference.

DETAILED DESCRIPTION OF THE INVENTION

The compounds of the invention are thiadiazoles of the structure

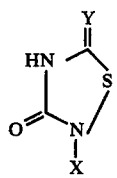

wherein Y is O, NH or NAc and; X is H, ribofuranosyl, 2-deoxyribofuranosyl or Ac-blocked ribofuranosyl and 2-deoxyribofuranosyl and; Ac is $C_1$-$C_8$ acyl; which are useful as antimicrobal agents.

In a select group of compounds Y is O, NH or NAc and; X is H, β-D-ribofuranosyl or 2,3,5-tri-O-Ac-β-D-ribofuranosyl where Ac is acetyl.

In a preferred group, which are useful as antimicrobal agent, Y is O and X is H or Y is NAcetyl and X is β-D-ribofuranosyl or 2,3,5-tri-O-acetyl--β-D-ribofuranosyl.

As shown in Scheme I the compounds of the invention are prepared by ring closure of monothiobiuret in the presence of hydrogen peroxide to 5-amino-1,2,4-thiadiazole-3-one (1).

1 can be deaminated to yield 1,2,4-thiadiazolin-3,5-dione (2) or it can be blocked with trimethylsilyl groups and reacted in the presence of $SnCl_4$ with either 1,2,3,5-tetra-O-acyl-β-D-ribofuranose or 1,2,5-tri-O-acyl-2-deoxy-D-ribofuranose to form 5-acetamido-1,2,4-Thiadiazole-3-one-acyl blocked nucleosides (4 and 5). Similarly 2 can be blocked with trimethylsilyl groups and reacted in the presence of $SnCl_4$ with 1,2,3,5-tetra-O-acyl-β-D-ribofuranose to form 1,2,4-thiadiazolin-3,5-dione-acyl-blocked nucleoside (6). In the case of nuceleoside 4, selective deblocking yields 5-acetamido-1,2-4-thiadiazole-3-one nucleoside (7). Complete deacylation of 5,6 and 7 yields, 1,2,4-thiadiazol-3,5-dione or 5-amino-1,2,4-thiadiazolin -3-one nucleosides (8,9,10 and 11).

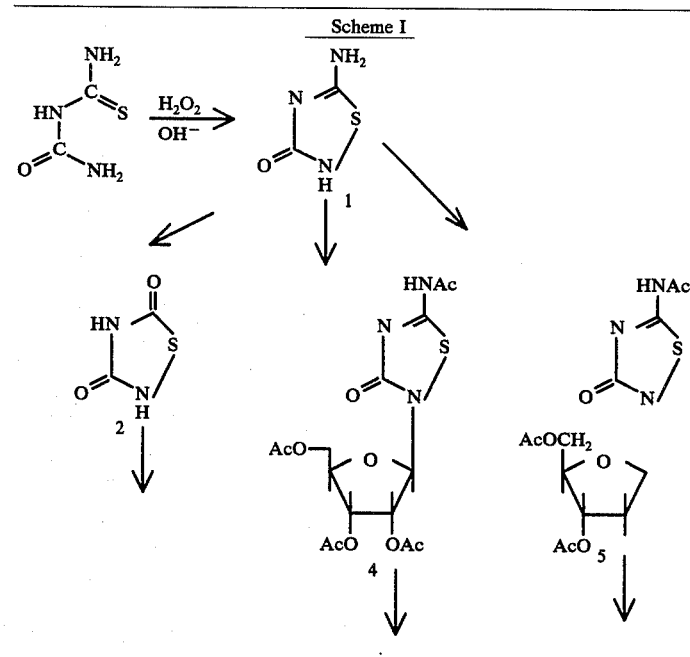

Scheme I

-continued

Scheme I

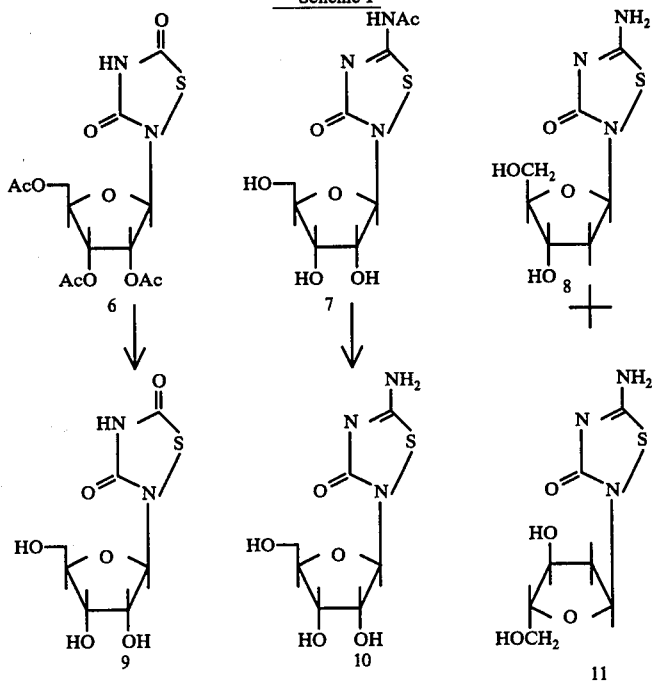

The following are representative examples of preparations of the compounds and determinations of antimicorbial activities.

EXAMPLE I

5-Amino-1,2,4-thiadiazol-3-one (1)

To an ice-cooled solution of monothiobiureth (15.0 g, 0.125 mole) in 2N sodium hydroxide (95 ml) was added 30% hydrogen peroxide (18.0 ml) dropwise with efficient stirring. After the reaction mixture was kept at 0° for 45 min it was carefully acidified with concentrated hydrochloric acid to pH 4.5. The white solid that separated was collected by filtration and crystallized from hot water as needles to yield 11.0 g (74.6%), m.p, 220°–222° (dec.). $^1$H nmr (Me$_2$SO-d$_6$) $\delta$8.38 (s, broad, NH$_2$); uv $\lambda$max (pH 1) 215 nm, sh ($\epsilon$ 5800), 248 (5700); $\lambda$max (pH 7) 217 nm ($\epsilon$ 10,500), 249 (4,700); $\lambda$max (pH 11) 218 nm, sh ($\epsilon$ 2100), 257 (5800).

Anal. Calcd for C$_2$H$_3$N$_3$OS (117.13): C, 20.50; H, 2.58; N, 35.87. Found: C, 20.51; H, 2.63; N, 35.70.

EXAMPLE II

5-Acetamido-2-(2,3,5-tri-O-acetyl-$\beta$-D-ribofuranosyl)-1,2,4-thiadiazol-3-one (4)

A mixture of dry 5-amino-1,2,4-thiadiazol-3-one (1 3.514 g, 0.03 mole, dried at 80° over P$_2$O$_5$ under vacuum, overnight), freshly distilled hexamethyldisilazane (10 ml) and a few crystals of ammonium sulfate (15 mg) was heated under reflux in anhydrous conditions for 2 hr. Within 20 min. a clear solution was obtained accompanied by a profusion of ammonia. After 2 hr the excess hexamethyldisilazane was removed by distillation under reduced pressure and the residual crystalline solid was used directly without further purification.

To a cold (5°–10°) solution of the above trimethylsilyl derivative in dry dichloroethane (150 ml) was added 1,2,3,5-tetra-O-acetyl-$\beta$-D-ribofuranose (9.543 g, 0.03 mole) followed by stannic chloride (10.94 g, 0.042 mole). The reaction mixture was protected from moisture and stirred for 5 hr at ambient temperature before the solvent was evaporated to dryness. The residue was held at full pump vacuum for 2 hr. The residual foam was dissolved in chloroform (100 ml) and slowly poured into 250 ml of cold, saturated aqueous sodium bicarbonate solution with stirring, keeping the mixture basic at all times. The resulting emulsion was filtered through a Celite pad which was washed with chloroform (5 $\times$ 30 ml). The combined organic layer washed again with water (2 $\times$ 100 ml) before it was dried over anhydrous sodium sulfate. The solvent was evaporated and the residual foam (9.2 g) was chromatographed on silica gel column (3.5 $\times$ 85 cms) prepacked in ethyl acetate and eluted with ethyl acetate: water:n-propanol (4:2:1, v/v, upper layer). The band containing the requisite product was collected and the solvent evaporated to leave 8.1 g of cream colored foam. The foam was triturated with cold anhydrous ether and the residual solid was crystallized from ethanol as needles to yield 7.51 g (60.0%), m.p. 229°–230°; [$\alpha$]$_D^{25}$ —41.5° (c 1.0, ethanol); $^1$H nmr (CDCl$_3$) $\delta$2.17 (d, 9H, OAc), 2.56 (s, 3H, —NAc), 6.06 (d, J=4.5 Hz, C$_{1'}$H); uv $\lambda$max (pH 1) 236 nm ($\epsilon$ 12,000), 275 sh (4,000); $\lambda$max (pH 7 and 11) 256 nm ($\epsilon$ 13,000), 278 sh (6500).

Anal. Calcd for C$_{15}$H$_{19}$N$_3$O$_9$S (417.49): C, 43.16; H, 4.58; N, 10.06. Found: C, 43.32; H, 4.80; N, 9.79.

EXAMPLE III

5-Acetamido-2-($\beta$-D-ribofuranosyl)-1,2,4-thiadiazol-3-one (7)

To a solution of 5-acetamido-2-(2,3,5-tri-O-acetyl-$\beta$-D-ribofuranosyl)-1,2,4-thiadiazol-3-one (4, 0.5 g, 0.0011 mole) in anhydrous methanol (25 ml) was added 1N sodium methoxide in methanol, till the pH of the solution was 8.5 and the resulting solution was stirred at ambient temperature for 2.5 hr. Within 40 min the secondary O-acetyl groups were removed and by the end of 2 hr all the O-acetyl groups were removed as judged by tlc. After the O-deacetylation was complete, the sodium ions were removed by stirring the reaction mixture with Amberlite IRC-50 (H+) resin (7.0 g, dry weight) for 15 min before the neutral solution, free from resin, was evaporated to dryness. The residual gum was chromatographed on a silica gel column (3 × 27 cms) using ethyl acetate:water:n-propanol (4:2:1), v/v, upper phase). The appropriate fractions were pooled, solvent evaporated and the residue crystallized from aqueous ethanol to yield 0.23 g (67.0%), m.p. 204°–205° (dec.); $[\alpha]_D^{25}$ −50.1° (c 1.0, water); $^1$H nmr (Me$_2$SO-d$_6$) δ2.28 (s, 3H, —NAc), 5.65 (d, J=5.0 Hz, C$_1$H); uv λmax (pH 1) 235 nm (ε 10,600), 275 (3500); λmax (pH 7) 254 nm (ε 9900), 277 sh (5400); λmax (pH 11) 254 nm (ε 12,700), 277 sh (5,900).

Anal. calcd for C$_9$H$_{13}$N$_3$O$_6$S (291.28): C, 37.11; H, 4.49; N, 14.42. Found: C, 36.90; H, 4.47; N, 14.38.

EXAMPLE IV

5-Amino-2-(β-D-ribofuranosyl)-1,2,4-thiadiazol-3-one (10)

To a solution of 5-acetamido-2-(2,3,5-tri-O-acetyl-β-D-ribofuranosyl)-1,2,4-thiadiazol-3-one (4,1.0 g) or 5-acetamido-2-(β-D-ribofuranosyl)-1,2,4-thiadiazol-3-one (7) in anhydrous methanol (50 ml) was added 1N sodium methozide in methanol, till the pH of the solution was 9.0 and the solution was stirred at 30° for several days. After the reaction was complete, the solution was neutralized by stirring for 15 min with Amberlite IRC-50 (H+) resin. The resin was filtered off and the filtrate was evaporated to dryness in vacuo. The residue was chromatographed on a silica gel column (2.5 × 45 cms) using ethylacetate:water:n-propanol (4:2:1), v/v, upper phase). The appropriate fractions were pooled, solvent evaporated and the reisdue crystallized from aaueous ethanol to yield 0.24 g (40.2%), m.p. > 240° (dec.); $^1$H nmr (Me$_2$SO-d$_6$) δ5.63 (d, J=4.5 Hz, C$_1$H); uv λmax (pH 1) 220 nm (ε 14,950), 273 (5000); λmax (pH 7) 220 nm (ε 13,950), 255 (6250); λmax (pH 11) 230 nm (ε 1,200), 278 sh (7500).

Anal. Calcd for C$_7$H$_{11}$N$_3$O$_5$S (249.24): C, 33.73; H, 4.44; N, 16.85. Found: C, 34.08; H, 4.72; N, 16.64.

EXAMPLE V 1,2,4-Thiadiazolin-3,5-dione (2).

To an ice-cold suspension of 5-amino-1,2,4-thiadiazol-3-one (1 1.17 g, 0.01 mole) in 10 ml of water containing glacial acetic acid (2 ml) was added sodium nitrite (0.9 g) in small portions. The reaction flask was loosely stoppered and stirred 2–3 hr in the ice-bath before it was stored overnight in the refrigerator. The pale yellow solid that separated was collected, washed with cold water (3 × 5 ml) and air-dried before it was crystallized from a large excess of boiling water to yield 0.53 g. An additional 80 mg was isolated from the above filtrate. The total yield was 0.61 g (51.7%), m.p. > 300° (dec.).

Anal. Calcd for C$_2$H$_2$N$_2$O$_2$S (118.11): C, 20.33; H, 1.70; N, 23.71. Found: C, 20.02; H, 2.18; N, 23.43.

EXAMPLE VI 2-(β-D-Ribofuranosyl)-1,2,4-thiadiazol-3,5-dione (9).

A mixture of dry 1,2,4-thiadiazolin-3,5-dione (2, 1.3 g, 0.011 mole, dried at 100° over P$_2$O$_5$ under vacuum, overnight), freshly distilled hexamethyldisilazane (3 ml) and a few crystals of ammonium sulfate (10 mg) was heated under reflux in anhydrous conditions for 2.5 hr. Within 20 min a clear solution was obtained accompanied by a profusion of ammonia. After the end of the reaction time, the excess of hexamethyldisilazane was removed by distillation under reduced pressure and the residual semi-solid (14) was used directly without further purification.

To a cold (0°–5°) solution of the above trimethylsilyl derivative in dry dichloroethane (75 ml) was added 1,2,3,5-tetra-O-acetyl-β-D-ribofuranose (3.5 g, 0.011 mole) followed by stannic chloride (3.15 g, 0.012 mole). The reaction mixture was protected from moisture and stirred overnight at ambient temperature before it was poured into 200 ml. of cold, saturated aqueous sodium bicarbonate solution containing 200 ml. of chloroform, with efficient stirring and keeping the mixture basic at all times. The organic layer was separated and washed with water (2 × 75 ml) before it was dried over anhydrous sodium sulfate. The solvent was evaporated and the residual foam was chromatographed on silica gel column (4 × 40 cms) using chloroform: methanol (95:5, v/v) as the solvent. The fractions containing the requisite product was collected and the solvent evaporated to leave 1.05 g of the blocked nucleoside 6, as pale yellow foam. To a solution of this blocked nucleoside in anhydrous methanol (25 ml) was added 1N sodium methoxide in methanol, till the pH of the solution was 9.0 and the reaction mixture was stirred at ambient temperature for 3 hr. The sodium ions were removed by stirring the reaction mixture with Amberlite IRC-50 (H+) (10 g, dry weight) for 20 min before the neutral solution, free from resin, was evaporated to dryness. The residual gum was purified on a preparative tlc plate (silica gel) using ethyl acetate:water:n-propanol (4:2:1, v/v upper phase) as the developer to yield 0.35 g (12.7%), m.p. 180°–182° (dec.); $[\alpha]_D^{25}$ − 32.4° (c 1.0, water); $^1$H nmr (Me$_2$SO-d$_6$/D$_2$O) δ5.62 (d, J=5.0 Hz, C$_1$H); uv λmax (pH 1) 235 nm (ε 7750), 276 (2850); λmax (pH 7 and 11) 253 nm (ε 7750), 278 sh (4400).

Anal. Calcd for C$_7$H$_{10}$N$_2$O$_6$S (250.23): C, 33.60; H, 4.02; N, 11.19. Found: C, 33.28; H, 3.47; N, 10.78.

EXAMPLE VII

5-Amino-2-(2-deoxy-α-D-ribofuranosyl)-1,2,4-thiadiazol-3-one (II) and 5-amino-2-(2-deoxy-β-D-ribofuranosyl)-1,2,4-thiadiazol-3-one (8).

5-Amino-1,2,4-thiadiazol-3-one (1, 2.0 g, 0.017 mole) was silylated as described in example II, and dissolved in dry dichloroethane (100 ml). 1,3,5-Tri-O-acetyl-2-deoxy-D-ribofuranose [M. J. Robins and R. K. Robins, J. Amer. Chem. Soc., 87, 4934 (1965); 4.4 g, 0.017 mole] in dichloroethane (25 ml) was added followed by stannic chloride (2.1 ml). The reaction mixture was protected from moisture and stirred at ambient temperature overnight, before it was poured into 250 ml of cold, saturated aqueous sodium bicarbonate solution containing 200 ml of chloroform keeping the mixture basic at all times. The organic layer was separated and washed with water (2 × 100 ml) before it was dried over anhydrous sodium sulfate. The solvent was evaporated to dryness and the residual gum was chromatographed on silica gel column (4 × 70 ml) using chloroform:methanol (95:5, v/v) as the solvent. The band carrying the products was collected and evaporated to dryness, leaving 0.4 g of gummy blocked anomeric nucleosides (5) which was dissolved in anhydrous methanol (25 ml). The methanolic solution was treated with 1N sodium methoxide in methanol till the pH of the solution was 8.5 and stirred at ambient temperature for 2 hr. The sodium ions were removed by stirring the reaction mixture with Amberlite IRC-50 (H$^+$) resin (5 g, dry weight) for 15 min before the neutral solution, free from resin, was evaporated to dryness. The residual gum was subjected to preparative tlc (silica gel) using ethyl acetate:water:n-propanol(4:2:1, v/v, upper phase) as the developer. The bands carrying the homogeneous products were eluted with the same solvent system and evaporated to dryness. The residue was crystallized from water to yield 80 mg of 5-amino-2-(2-deoxy-α-D-ribofuranosyl)-1,2,4-thiadiazol-3-one (11), m.p. > 150° (dec.) $^1$H nmr (Me$_2$SO-d$_6$) multiplet of four centered at δ6.1 and other protons.

Anal. Calcd for C$_7$H$_{11}$N$_3$O$_4$S (233.24): C, 36.04; H, 4.75; N, 18.01. Found: C, 35.51; H, 4.32; N, 18.57. 5-Amino-2-(2-deoxy-β-D-ribofuranosyl)-1,2,4-thiadiazol-3-one (8) was crystallized from water as hygroscopic solid, 62 mg, m.p. > 160° (dec.); $^1$H nmr (Me$_2$SO-d$_6$) pseudo-triplet centered at δ6.08 and other protons Anal. Calcd for C$_7$H$_{11}$N$_3$O$_4$S (233.24): C, 36.04; H, 4.75; N, 18.01. Found: C, 35.82; H, 5.28; N, 18.63.

EXAMPLE VIII

The compounds of the invention were assayed for antimicrobal activity. Their minimal inhibitory concentration was determined against test strains of bacteria, yeast and mold. The bacteria used were *Klebsiella pneumonia* (Kp) and *Staphylococcus aurens* (Sa). *Candida Albicans* (Ca) was chosen as a representative yeast and *Trichophyton mentagrophytes* (Tm) as a representative mold.

The in vitro sensitivity of these organisms to the compounds of the invention were quantitatively determined by both dilution assay procedures. Serial dilutions were prepared in a "Chemically defined medium" as prepared by P. F. Dougherty etal., *Antimicrobial Agents* and *Chemotherapy*, December 1976 p. 923–925 expressly incorporated herein by reference.

The activity of the compounds are expressed as the minimal inhibitory concentration (MIC), expressed as μmol/ml. which was the highest dilution of the compound which prevented visible growth of the pathogen. Bacterial and yeast MIC's were read following 24 hours of incubation at 35° C. Dermatophyte inhibition was read after 48 hours of incubation at 30° C.

The results of these tests demonstrated that compound 4 has a MIC of 0.4 against Sa, 0.32 against Ca and 0.32 against Tm. Compound 7 has a MIC of 0.4 against Sa Compound 2 has a MIC of 0.08 against Kp, 0.08 against Sa, 0.08 against Ca and 0.04 against Tm.

We claim:
1. The compound 1,2,4-Thiadiazolidine-3,5-dione.